United States Patent
Wu

(10) Patent No.: US 6,622,546 B2
(45) Date of Patent: Sep. 23, 2003

(54) MOISTURE CONTENT TESTER FOR NON-DESTRUCTIVE MULTIPURPOSE TESTING

(76) Inventor: Juen-Kong Wu, No. 43, Chung San Rd., SanShing Hsiang, I-Lan Hsien (TW)

( * ) Notice: Subject to any disclaimer, the term of this patent is extended or adjusted under 35 U.S.C. 154(b) by 0 days.

(21) Appl. No.: 10/023,980

(22) Filed: Dec. 21, 2001

(65) Prior Publication Data

US 2003/0115938 A1 Jun. 26, 2003

(51) Int. Cl.[7] .......................... G01N 25/56; G01R 27/26
(52) U.S. Cl. .............................. 73/73; 73/74; 324/689; 324/690
(58) Field of Search .................... 73/73, 74, 335.03, 73/335.04, 29.05; 324/689, 690

(56) References Cited

U.S. PATENT DOCUMENTS

| | | | | |
|---|---|---|---|---|
| 3,296,524 A | * | 1/1967 | Updegraff | 324/689 |
| 4,399,404 A | * | 8/1983 | Resh | 324/689 |
| 4,540,936 A | * | 9/1985 | Walsh | 324/690 |
| 4,909,070 A | * | 3/1990 | Smith | 73/73 |
| 4,929,885 A | * | 5/1990 | Dishman | 324/690 |
| 5,092,819 A | * | 3/1992 | Schroeder et al. | 460/7 |
| 5,231,358 A | * | 7/1993 | Kapsokavathis et al. | 324/690 |
| 5,424,649 A | * | 6/1995 | Gluck et al. | 324/690 |
| 5,479,104 A | * | 12/1995 | Cambell | 324/690 |
| 5,852,368 A | * | 12/1998 | Larsen | 324/689 |
| 5,859,536 A | * | 1/1999 | Stockton | 324/690 |
| 5,861,755 A | * | 1/1999 | Moerk et al. | 324/690 |
| 6,327,899 B1 | * | 12/2001 | Diekhans et al. | 73/73 |

FOREIGN PATENT DOCUMENTS

| | | | | |
|---|---|---|---|---|
| EP | 571115 A2 | * | 5/1992 | 324/689 |
| GB | 2083663 A | * | 3/1982 | |

* cited by examiner

Primary Examiner—Edward Lefkowitz
Assistant Examiner—Michael Cygan
(74) Attorney, Agent, or Firm—Troxell Law Office PLLC

(57) ABSTRACT

A moisture content tester for non-destructive multipurpose testing that may be arranged in a drying apparatus or a testing box for proceeding a test of moisture content for an object to be tested and further have setting function for instructable water-containing rate is comprised of shell body, circuit plate, temperature compensation temperature-sensing bar, emitting pole, receiving pole, and controlling unit. A high frequency is emitted from the emitting pole and received by the receiving pole. Again, the received high frequency (sawtooth waveform) signal is transferred to the controlling unit through the circuit plate. The controlling unit then calculates the value of moisture content according to the received high frequency signal and the temperature value measured by the temperature compensation temperature-sensing bar. Further, the drying motion or displayed water-containing rate of the drying apparatus is controlled according to the value of moisture content.

4 Claims, 14 Drawing Sheets

MOISTURE CONTENT TESTER FOR NON-DESTRUCTIVE MULTIPURPOSE TESTING

FIELD OF THE INVENTION

The present utility model is to provide a moisture content tester for non-destructive multipurpose testing, especially to a kind of moisture content tester adapted for drying apparatus for granular or liquid object such as cereals, sand stone, or plastic particle. etc.

BACKGROUND OF THE INVENTION

Accordingly, a general crop such as cereals and so forth all needs to be dried first after being harvested and then is proceeded a long time storage and keeping. Nowadays, it is very popular to apply drying apparatus to dry cereals with hot air generated by stove. However, in the mean time, during the process of drying, it is necessary to test the moisture content of the cereals at uncertain time or in continuity, so that it may prevent cereals from being moldy or rotten because of insufficient drying, or avoid wasting energy because of over-drying.

SUMMARY OF THE INVENTION

Therefore, the object of the present utility model is to provide a moisture content tester for non-destructive multipurpose testing that may have non-destructive testing function, be capable of continuous testing, have low breakdown rate, have multipurpose and high common use, be able to match and control the motion of drying apparatus, have setting function for instructable water-containing rate, and be adapted for larger scope of water-containing test, etc.

The secondary object of the present utility model is to provide a kind of moisture content tester for material-handling apparatus, which may send the object already been tested out the apparatus through the material-exhausting apparatus.

DETAILED DESCRIPTION OF THE PREFERRED EMBODIMENTS

Figure 1:
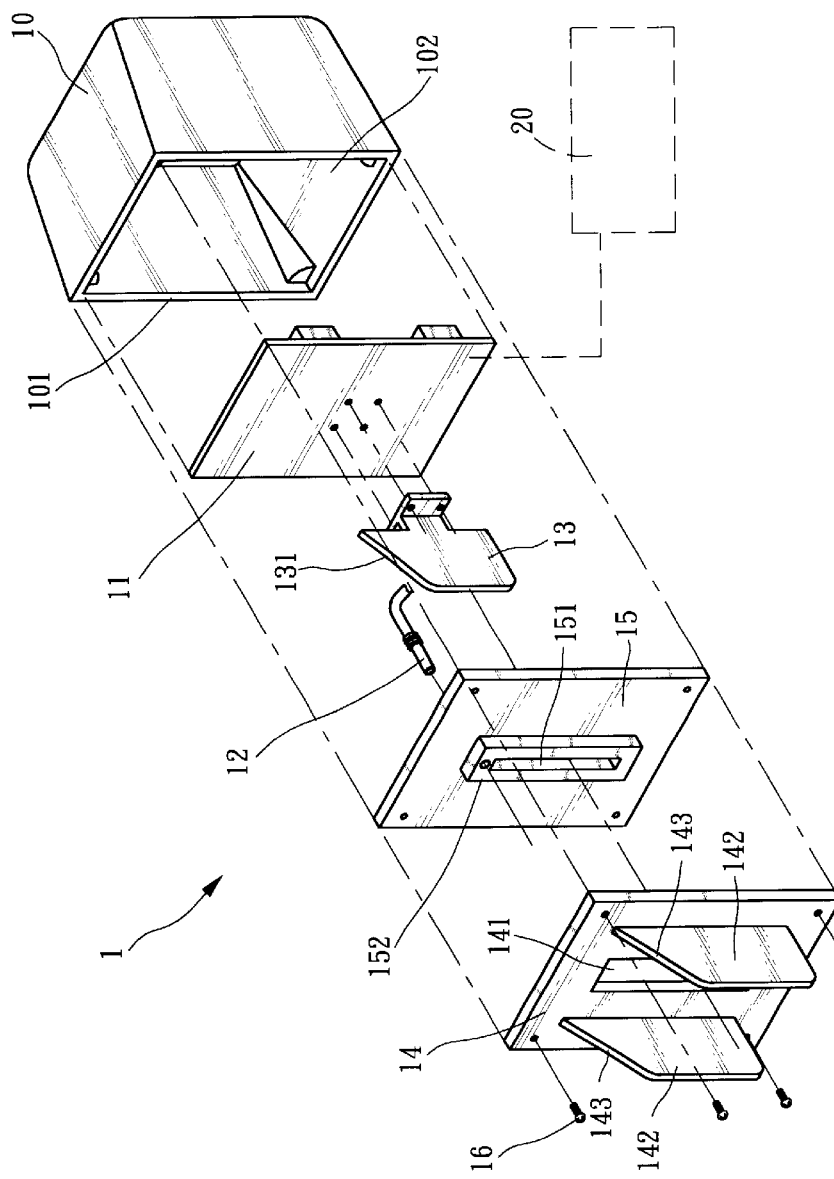
FIG. 1 is a three-dimensional illustration for the exploded elements for a preferable embodiment of the moisture content tester according to the present utility model.
Figure 2:
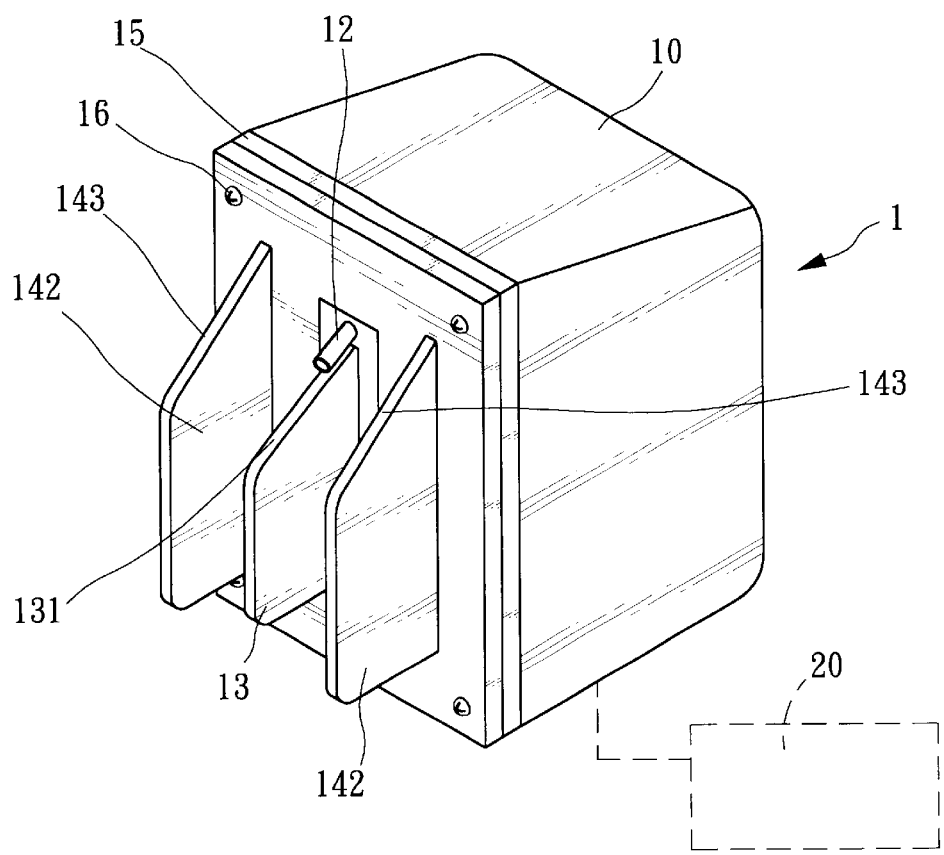
FIG. 2 is a three-dimensional assembly view for the moisture content tester shown in FIG. 1.

Please refer to FIG. 1 and FIG. 2, which show a preferable embodiment of the moisture content tester for non-destructive multipurpose testing 1 according to the present utility model that may be arranged in a machine or apparatus (e.g. cereals drying apparatus) to conduct a moisture content test on an object (e.g. cereals) to determine water containment. In this preferable embodiment, the moisture content tester 1 includes: a shell body 10, a circuit plate 11, a temperature compensation temperature-sensing bar 12, at least one emitting pole 13, at least one receiving pole 14, an insulation plate 15, and a controlling unit 20.

One side of the shell body 10 is under opening state and is an opening side 101, the interior of which is a hollow accommodation space 102.

The circuit plate 11 is accommodated in the accommodation space 102 of the interior of the shell body 10. A circuit design (not shown in the drawings) can at least be arranged on the circuit plate 11 for processing temperature sensing data, generating high frequency, and receiving high frequency, and so forth. One end of the temperature compensation temperature-sensing bar 12 is connected onto the circuit plate 11, and another end is protruded out the shell body 10 through the opening side 101 for processing the sensing of temperature value.

The emitting pole 13 is formed as a fin structure, one end of which is connected (coupled and fixed) onto the circuit plate 11, and another end is protruded out the shell body 10 through the opening side 101. Further, the upper side of the emitting pole 13 is designed as an inclining side 131, the function of which will be described hereinafter. The emitting pole 13 is coupled onto the circuit that may generate high frequency that may be emitted out from the emitting pole 13.

The receiving pole 14 is formed as a covering plate structure, which may just be covered on the opening side 101 of the shell body 10. An opening 141 and at least one protruding fin 142 with thin plate form are arranged on the receiving pole 14. The fin 142 is larger than the emitting pole 13. Further, an inclining edge 143 is also arranged on the upper side of the fin 142. The position and form of the opening 141 is matched with the emitting pole 13 to provide it to protrude through the receiving pole 13. The protruding out direction of the fin 142 is matched with the emitting pole 13 and kept with an appropriate interval with the emitting pole 13. The receiving pole 14 is coupled to the circuit capable of receiving high frequency. The high frequency emitted from the emitting pole 13 may be received by the fin 142 of the receiving pole 14 and converted into high frequency signals (capacitance signals) by the circuit that is arranged on the circuit plate 11 and can receive the high frequency.

The insulation plate 15 is located between the receiving pole 14 and the circuit plate 11. An opening groove 151 is arranged at one position on the insulation plate 15 corresponding to the emitting pole 13 for providing the emitting pole 13 to protrude through the insulation plate 15. The circumference of the opening groove 151 is further arranged with protruding edge 152 that may just be set in between the opening 141 of the receiving pole 14 and the emitting pole 13 to prevent the direct contact between the emitting pole 13 and the receiving pole 14. As regards to the inter-connection among the insulation plate 15, receiving pole 14, and shell body 10, they may be locked by screws 16, or melted and pasted by other manners for being connected integrally to one body.

Figure 3:
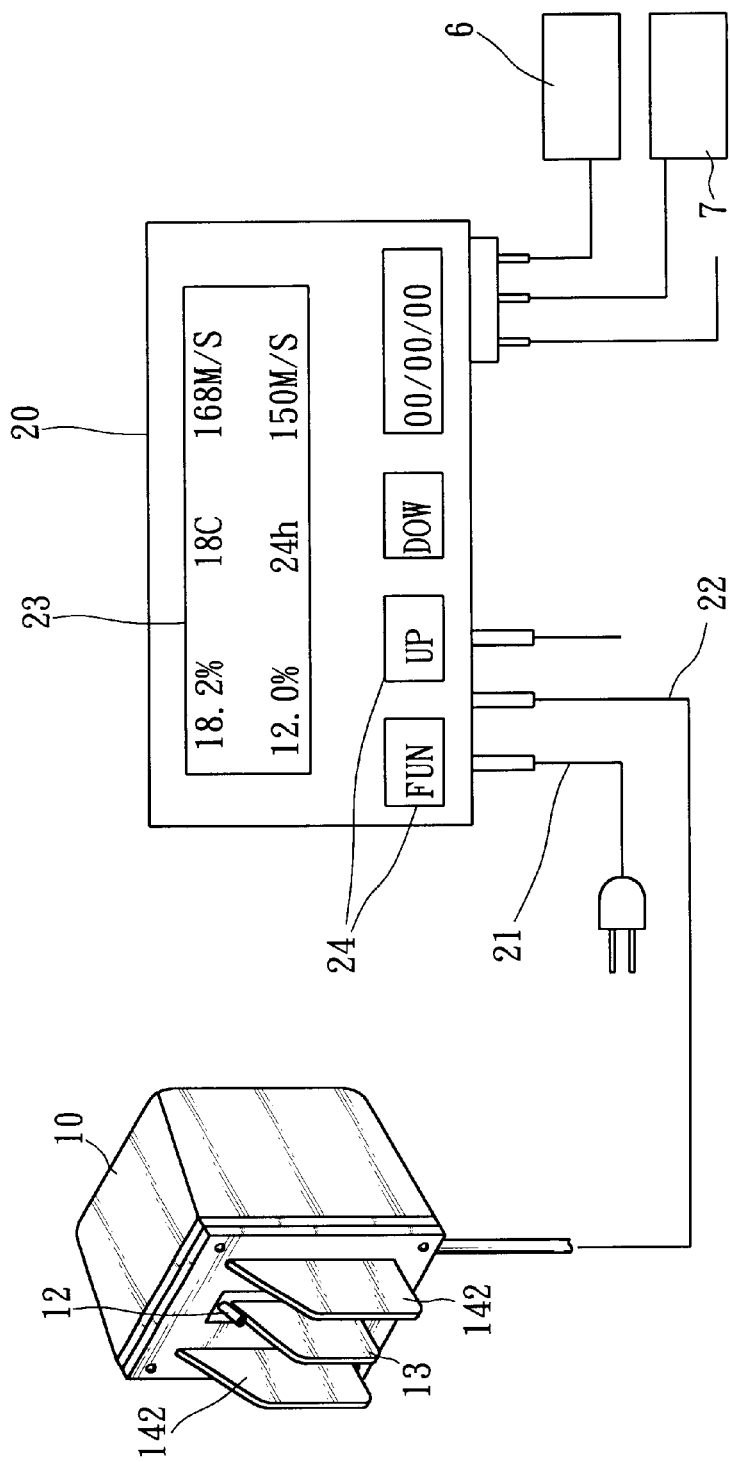
FIG. 3 is an implementing view for the controlling unit of the moisture content tester according to the present utility model.

Please refer to FIG. 3. The controlling unit 20 is respectively connected to a power source (not shown in the drawings) and a circuit plate 11 by a power line 21 and a connection line 22. The high frequency signals received by the receiving pole 14 and the temperature value signals sensed by the temperature compensation temperature-sensing bar 12 both may be transferred respectively to the controlling unit 21 through the circuit plate 11 and the connection line 22. The corresponding water containment value may be calculated out by both the circuit and software design in the controlling unit 20 according to the high frequency signals (capacitance signals) and by matching with the signals of temperature value.

Figure 4A:
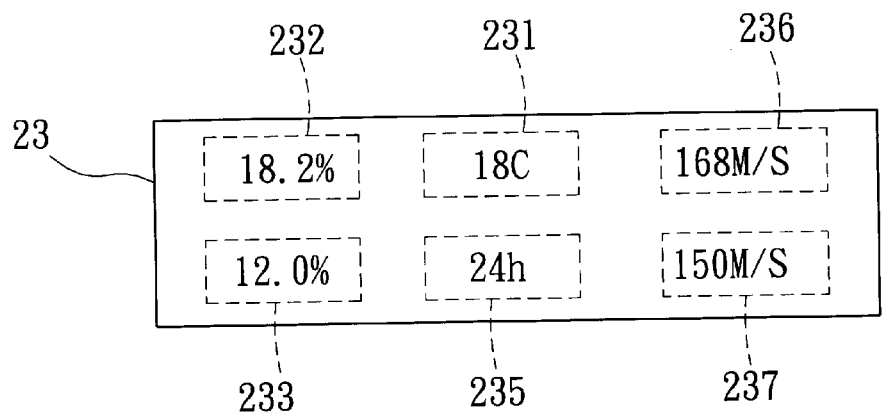
FIG. 4A is an embodiment for displaying data for the displaying unit according to the present utility model.
Figure 4B:
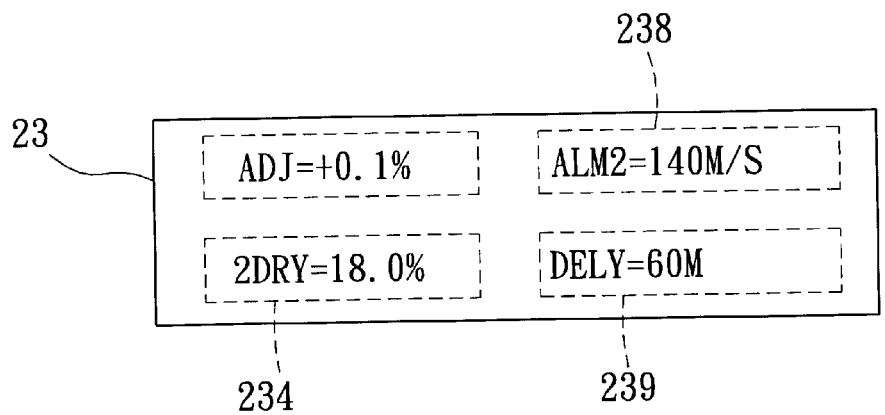
FIG. 4B is another embodiment for displaying data for the displaying unit according to the present utility model.

A displaying unit 23 and several controlling keys 24 are further arranged on the controlling unit 20. As shown in FIG. 4A and FIG. 4B, in this preferable embodiment, the displaying contents of the displaying unit 23 may include: the temperature value 231 of the object to be tested that is measured by the temperature compensation temperature-sensing bar, water containment value 232 calculated by the controlling unit 20, a first predetermined water containment value 233 (used for designating when to stop drying), a second predetermined water containment value 234 (used for designating when to increase drying power), a time-setting value 235 (used for setting time for machine shutdown), a measured wind power value 236, a first determined wind power value 237 (used for sending off alarm), a second predetermined wind power value 238 (used for shutting the machine down forcedly), and a time-delaying value 239 (used for delaying the shutdown time of the fan after the stop of machine). In this preferable embodiment, it is impossible to delay above-mentioned values all at once, because of the size limitation of the displaying unit 23, and therefore each data value is displayed in batches by pressing the controlling key 24. Of course, we may also change the design of the displaying unit 23 to show above-mentioned values all at once on the displaying unit 23.

Figure 6:
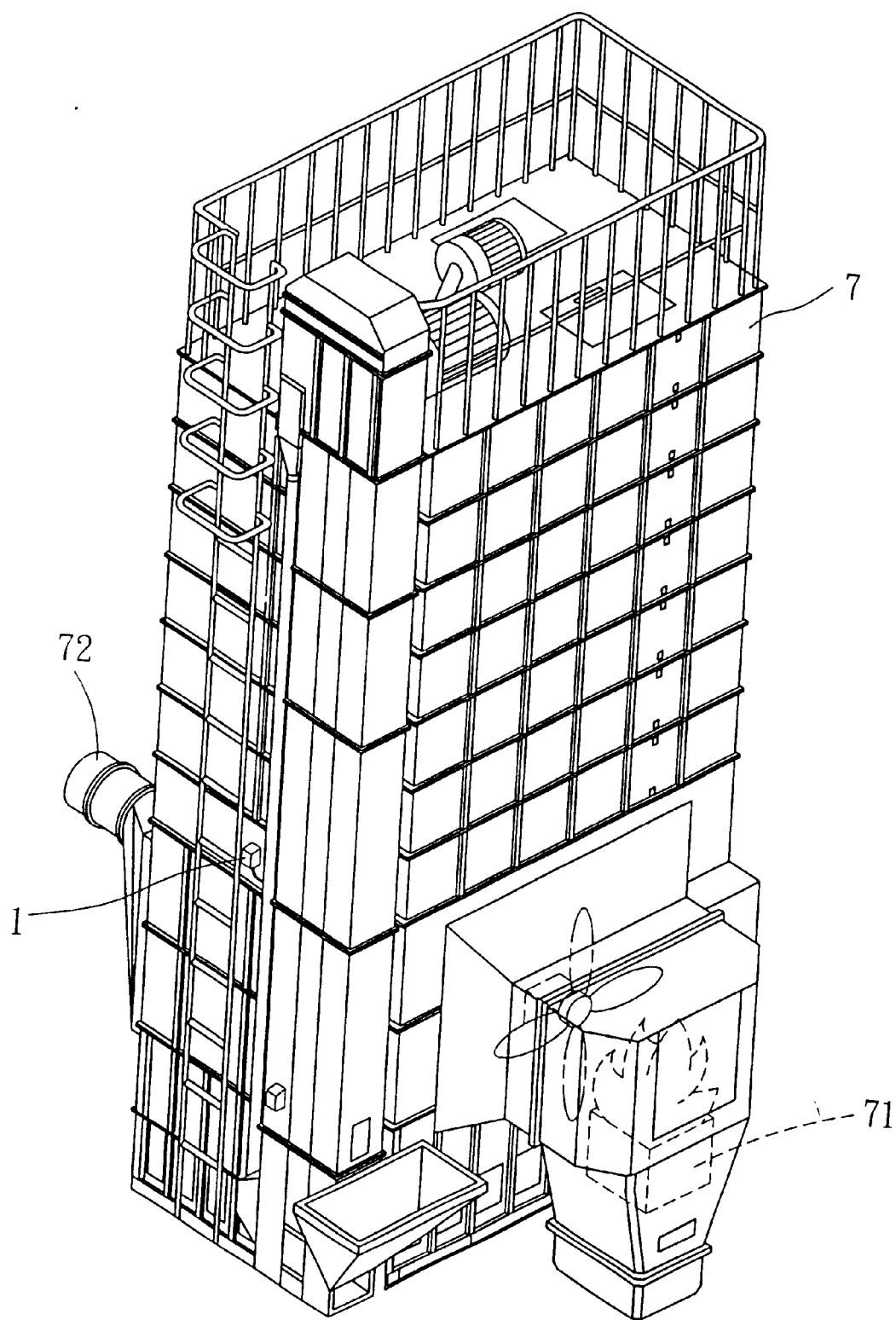
FIG. 6 is a three-dimensional illustration for the moisture content tester according to the present utility model arranged in a cereals drying apparatus.
Figure 7:
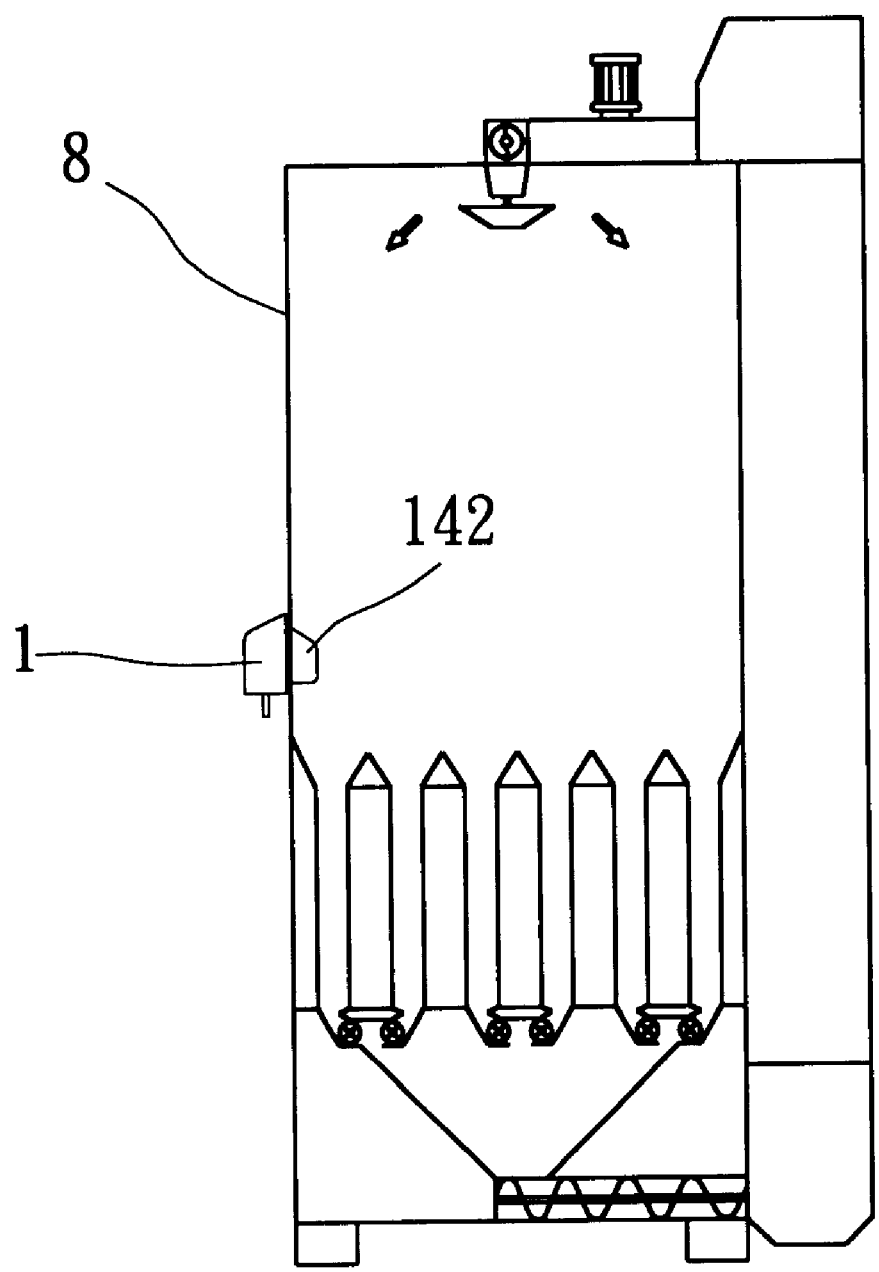
FIG. 7 is another cross-sectional illustration for the moisture content tester according to the present utility model arranged in another cereals drying apparatus.
Figure 8:
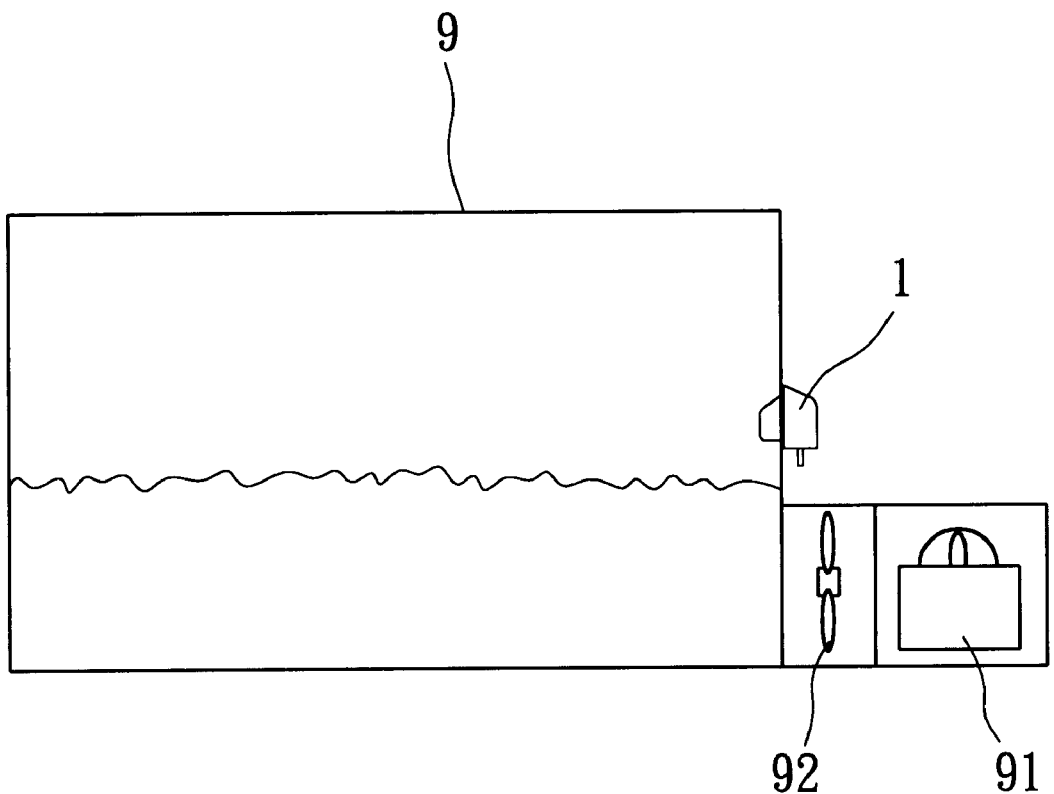
FIG. 8 is an implementing illustration for the moisture content tester according to the present utility model arranged in further another cereals drying apparatus.
Figure 9:
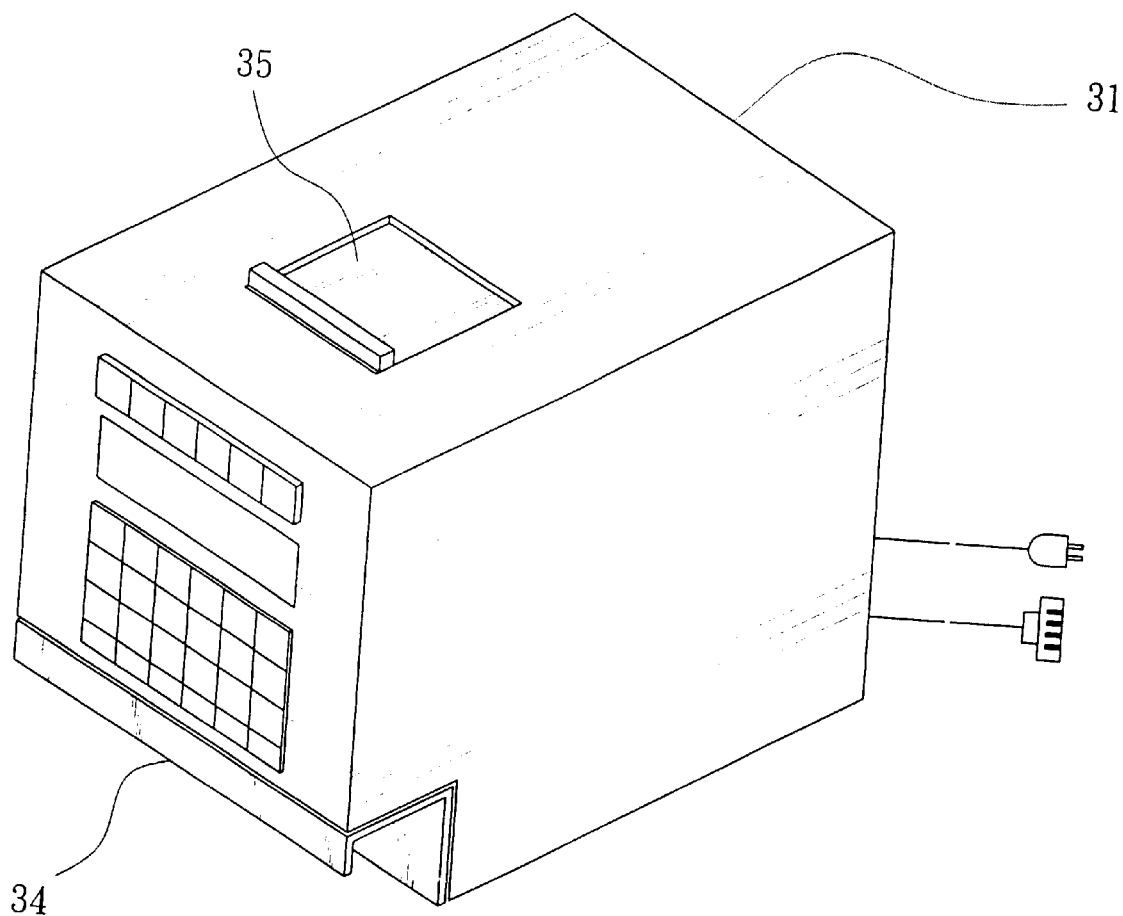
FIG. 9 is an outer appearance view for the material-handling apparatus of the moisture content tester of another embodiment according to the present utility model.
Figure 10:
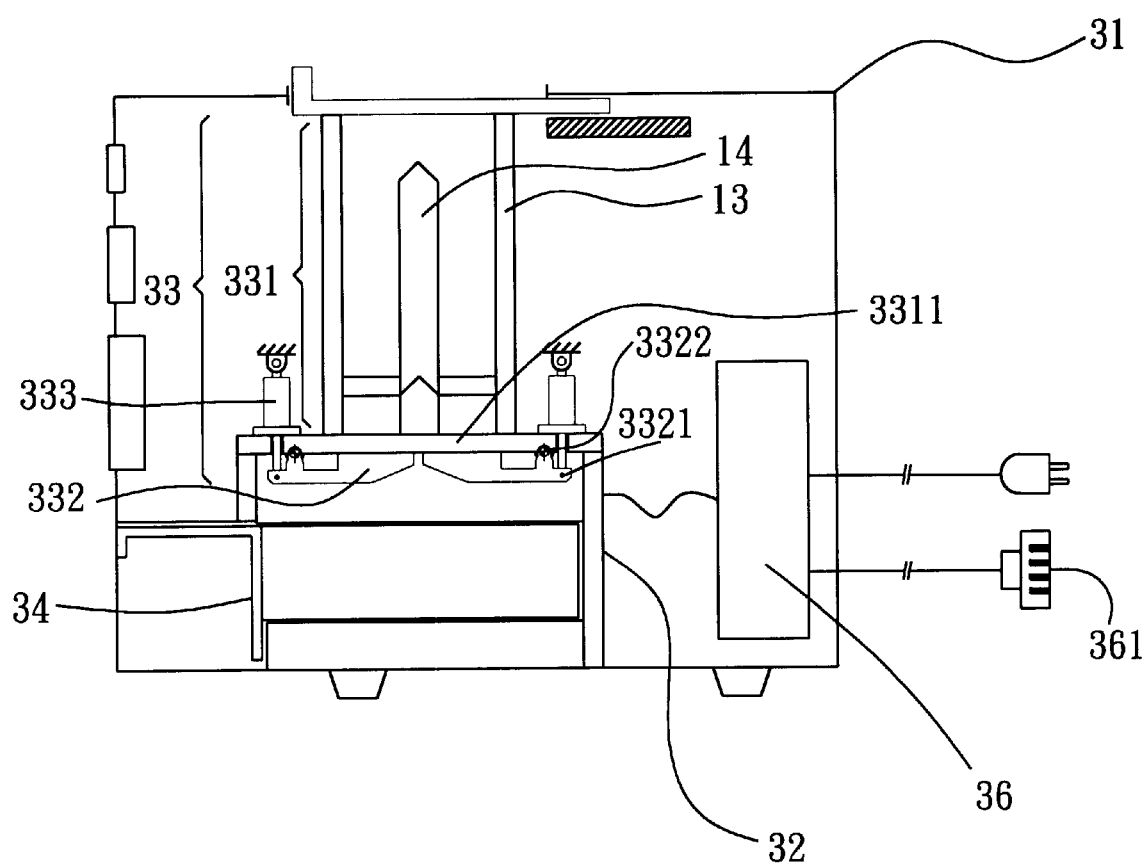
FIG. 10 is an interior structure illustration for the material-handling apparatus of the moisture content tester of another embodiment according to the present utility model.
Figure 11:
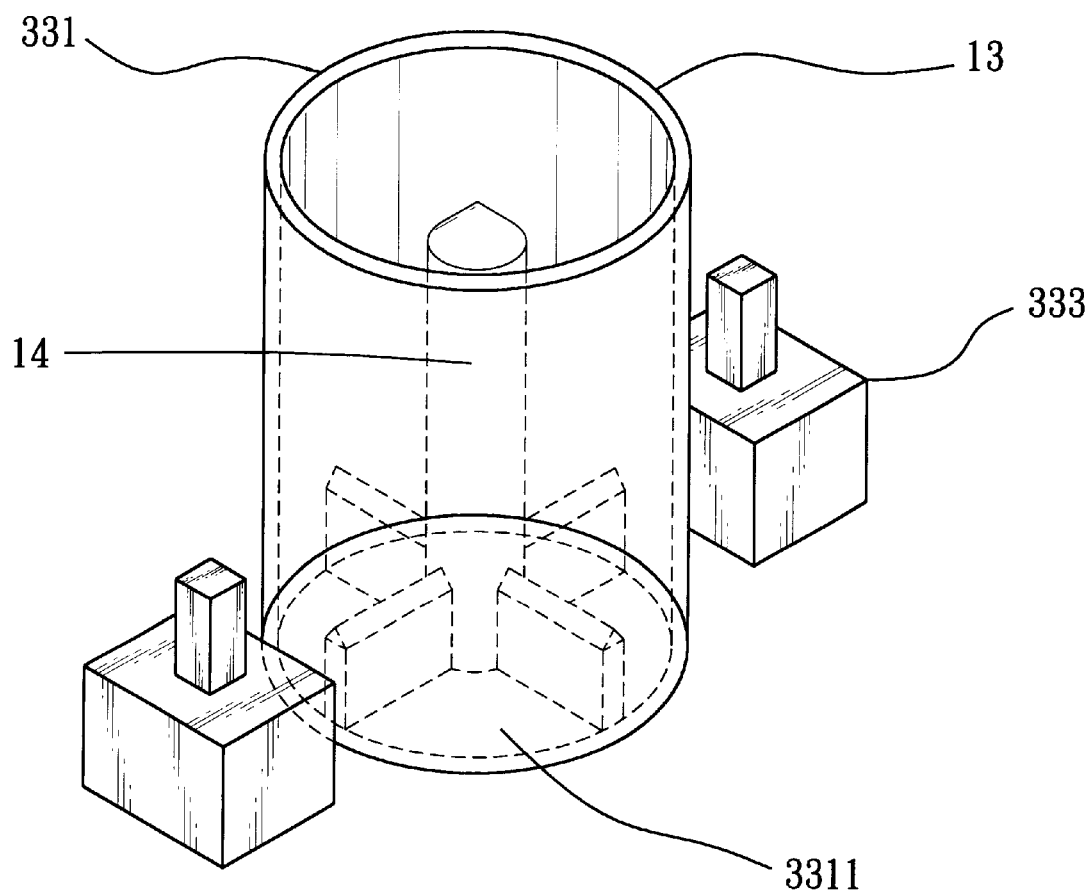
FIG. 11 is the material-feeding dipper of the material-handling apparatus of the moisture content tester of another embodiment according to the present utility model.
Figure 12A:
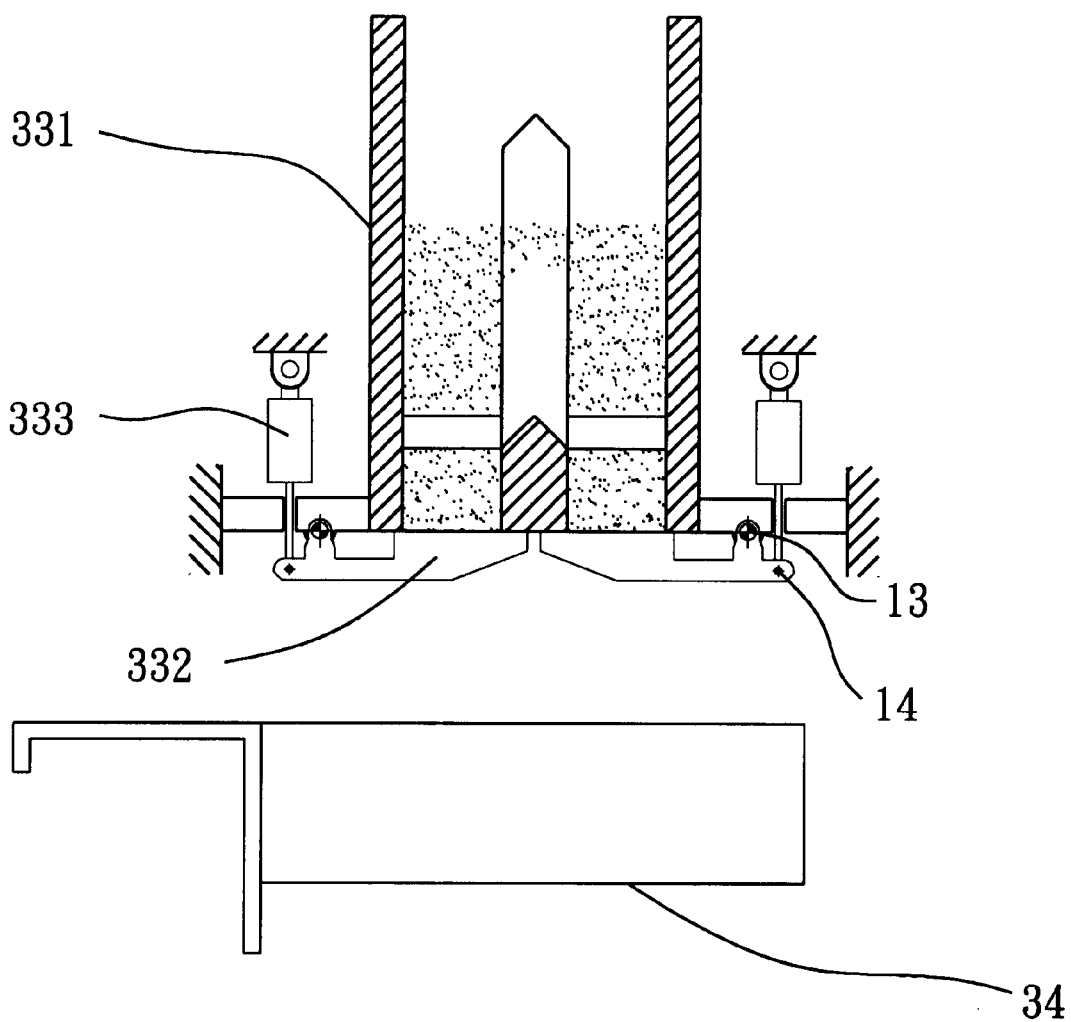
FIG. 12A is a motion (under the state of being tested) illustration for the material-handling apparatus of the moisture content tester of another embodiment according to the present utility model.
Figure 12B:
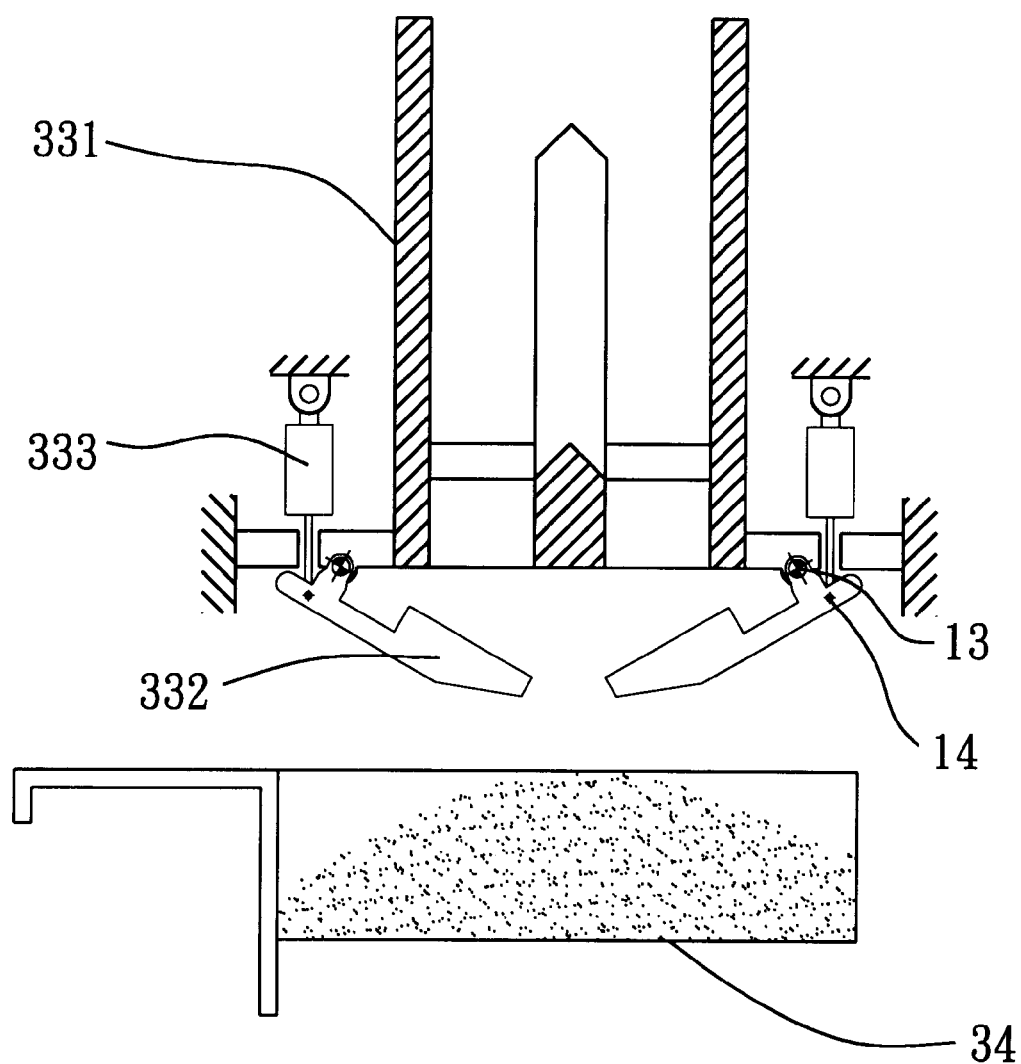
FIG. 12B is a motion (under the state of exhausting material) illustration for the material-handling apparatus of the moisture content tester of another embodiment according to the present utility model.

Please refer to FIG. 6 through FIG. 8, which are embodiment views of the moisture content tester according to the present utility model provided in the cereals drying apparatus 7, 8, 9 formed in various types (may be circulation-typed drying apparatus or fixation-typed drying apparatus). Generally speaking, in the drying apparatus 7, 8, 9, each is at least arranged with stoves 71, 91 and fans 72, 92. The hot air generated by the stoves 71, 91 is blown into (or may be sucked into) the drying apparatus 7, 8, 9 by the fans 72, 92 for proceeding drying motion on the objects to be tested that are accommodated therein. By arranging an opening (not assigned number in the drawings) of which the size is slightly smaller than that of the shell body 10 of the moisture content tester 1 at an appropriate position on each drying apparatus 7, 8, 9, the shell body 10 of the moisture content tester 1 is fixed at the circumference of the opening, and the fins 142 of the emitting pole 13 and the receiving pole 14 are extended into the interiors of the drying apparatus 7, 8, 9 for proceeding moisture content testing motion for the objects to be tested that are in the interiors of the drying apparatus 7, 8, 9. As regards to the positions of the drying apparatus 7, 8, 9, in which the moisture content testers 1 are arranged, generally speaking, as long as the emitting pole 13 and the receiving pole 14 may be covered by the objects to be tested such as cereals, but in the mean time, it also should be noted that the original functions of the drying apparatus for cereals are not influenced by these arrangements. That is, since the fin 142 of the emitting pole 13 and the receiving pole 14 will be covered by the cereals falling down, so in order to prevent the cereals, cereals bits, or cereals dusts from being accumulated on the emitting pole 13 and fin 142, therefore the emitting pole 13 and fin 142 are all designed as thin plate structures, of which the upper sides are also designed as inclining sides 131, 143 for facilitating the smooth falling down for the cereals, cereals bits, or cereals dusts, and so forth.

Figure 5:
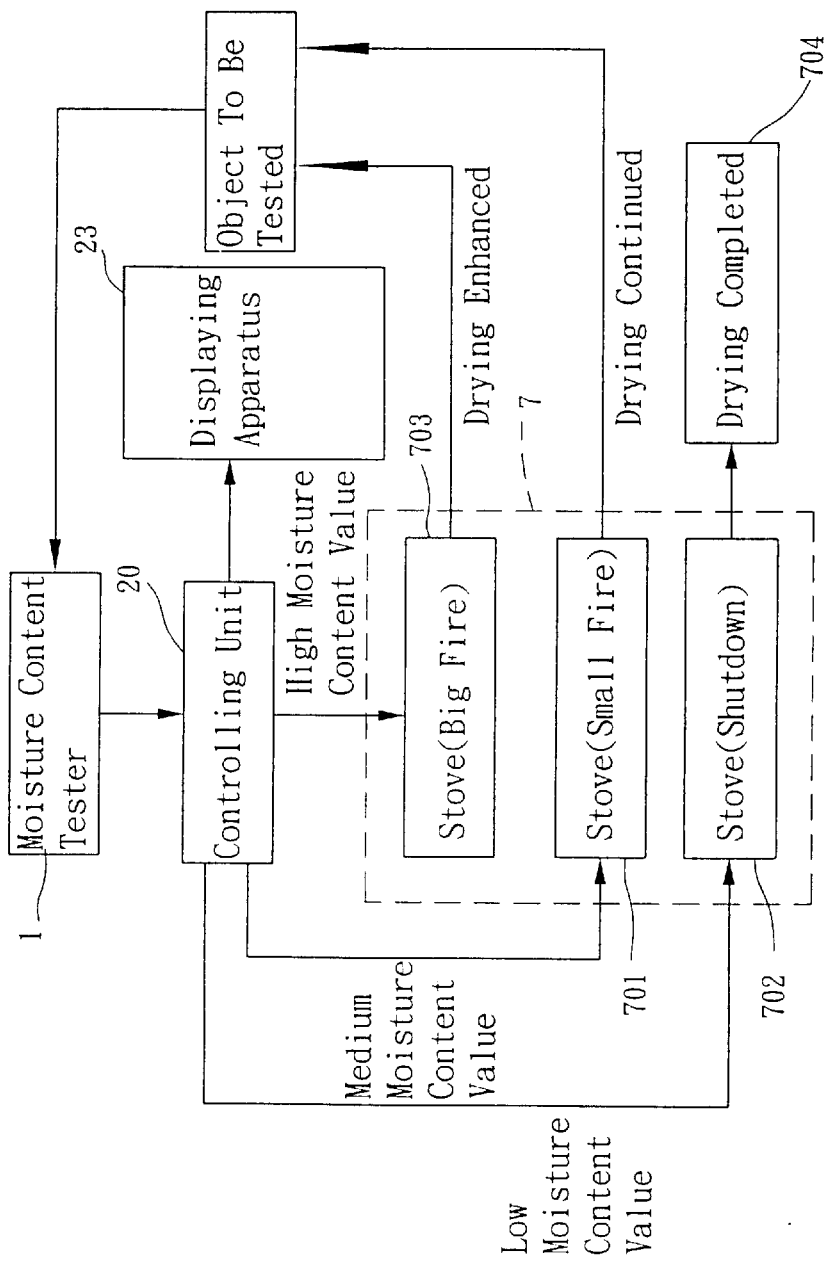
FIG. 5 is a flow chart for a drying apparatus' controlling motion proceeded by the controlling unit of the present utility model according to the measured water containment value.

Please refer to FIG. 5, which is a flowchart schematically describing a simple embodiment for the controlling motion of the drying apparatus 7 that is proceeded according to the measured water containment value and by the controlling unit 20 of the present utility model. The controlling unit 20 is further connected onto the drying apparatus 7 to control the drying motion of the drying apparatus 7 according to the water containment value measured by the moisture content tester 1. The temperature value 231 of the object to be tested by the moisture content tester 1 and the water containment value 232 (please refer to FIG. 4A and FIG. 4B) are received by the controlling unit 20 of the present utility model and displayed on the displaying unit 23. The first predetermined water containment value 233 is represented a preset degree till which the drying process will be stopped. When the water containment value 232 is higher than the first predetermined water containment value 233, the drying motion will be continuously proceeded (block 701) until the measured water containment value 232 is smaller than the first predetermined water containment value 233, and then the drying motion is stopped (block 702), and it represented that the drying process is completed (block 704). Under certain states, because the water containment amount of the cereals is higher, then it is possible to apply a dry air with higher temperature for proceeding the drying for raising up the efficiency. For example, when the water containment value 232 is higher than the second predetermined water containment value 234 (block 703), the controlling unit 20 will increase the firepower output of the stove 71 that controls the drying apparatus 7 for cereals for enhancing the drying speed.

Further, in order to prevent the hot air path of the drying apparatus 7 from being blocked sometimes by the accumulation of powder dusts or other factors to cause the hot air blown by the fan 72 unable to flow smoothly and the temperature of the stove 71 being too high to incur hazard, therefore the controlling unit 20 according to the present utility model has designed several data such as a measured wind power value 236, a first predetermined wind power value 237, a second predetermined wind power value 238, and so forth. The measured wind power value 236 is measured from the flowing speed of the dry hot air by a wind power measuring device 72 that is arranged in the flow path (not shown in the drawings) of hot air in the interior of the drying apparatus 7. When the measured wind power value 236 is smaller than the first predetermined wind power value 237, it indicates that the flow path of the hot air could be blocked partly, and at this time, the controlling unit 20 will send off alarm signals (such as alarm sound or flashing light, etc.) to notify the operator to carry out the dredging or maintenance job for the drying apparatus 7. While the measured wind power value 236 is smaller than the second predetermined wind power value 238, it represents that the flow path of the hot air may be blocked further seriously, and at this time, the controlling unit 20 will send off a further serious alarm signal or even stop the drying motion of the drying apparatus 7 directly for avoiding the incurrence of hazard. As regards to the delaying time value 239, it represents the fan 72 will be kept running for a specific time period until being stopped after the drying apparatus has been stopped.

In addition, the controlling unit 20 according to the present utility model may be further connected to a computer unit 6 (as shown in FIG. 3) for transferring the data measured and calculated by the controlling unit 20 to the computer unit 6. These data may further be processed by the computer unit 6, such as: storing, analyzing, printing out, plotting, or outputting from printer, etc.

Another embodiment according to the present utility model is carried out on a single testing machine.

Please refer to FIG. 9 through FIG. 12.

A kind of material-handling apparatus 33 of the moisture content tester according to the present utility model includes: a machine shell 31, a supporting rack 32, a material-handling apparatus 33, and a material-exhausting dipper 34.

The supporting rack 32 is arranged in the machine shell 31.

The material-handing apparatus 33 arranged at the upper portion of the supporting rack 32 includes a material-feeding dipper 331 that accommodates the object to be tested (cereals) and has an emitting pole 13, a receiving pole 14, and a lower opening 3311. The emitting pole 13 emits a high frequency wave that is received by the receiving pole 14. The moisture content of the object to be tested may be measured by the capacitance difference between two poles. The lower opening 3311 may remove the object to be tested therefrom. The material-handling apparatus 33 further includes at least a material-blocking lid 332, which may be used for opening and closing the lower opening 3311. And, the material-handling dipper is used for receiving the object to be tested that is exhausted from the material-feeding dipper 331.

Preferably, the material-handling apparatus 33 further includes at least one electromagnetic device 333 and one material-blocking lid 332 that has a connection end 3321 and a rotation axle 3322. The electromagnetic device 333 is arranged at the upper portion of the supporting rack 32 and at one side of the material-feeding dipper 331. The connection end 3321 of the material-blocking lid 332 is connected with the electromagnetic device 333. The rotation axle 3322 is fixed at the supporting rack 32. The electromagnetic device 333 is actuated to execute the opening and closing motions for the material-blocking lid 332 by taking the rotation axle 3322 that is fixed at the supporting rack 32 as its rotation axle.

However, within the same spirit of the present utility model, the formation for the opening and closing motions of lower material-blocking lid 332 may also be other types.

First one, the material-blocking lid 332 is a flat plate, which may be a side-pulling type for opening and closing. The material-blocking lid 332 makes a linear motion inside a rail and is driven by a driving unit.

Figure 13:
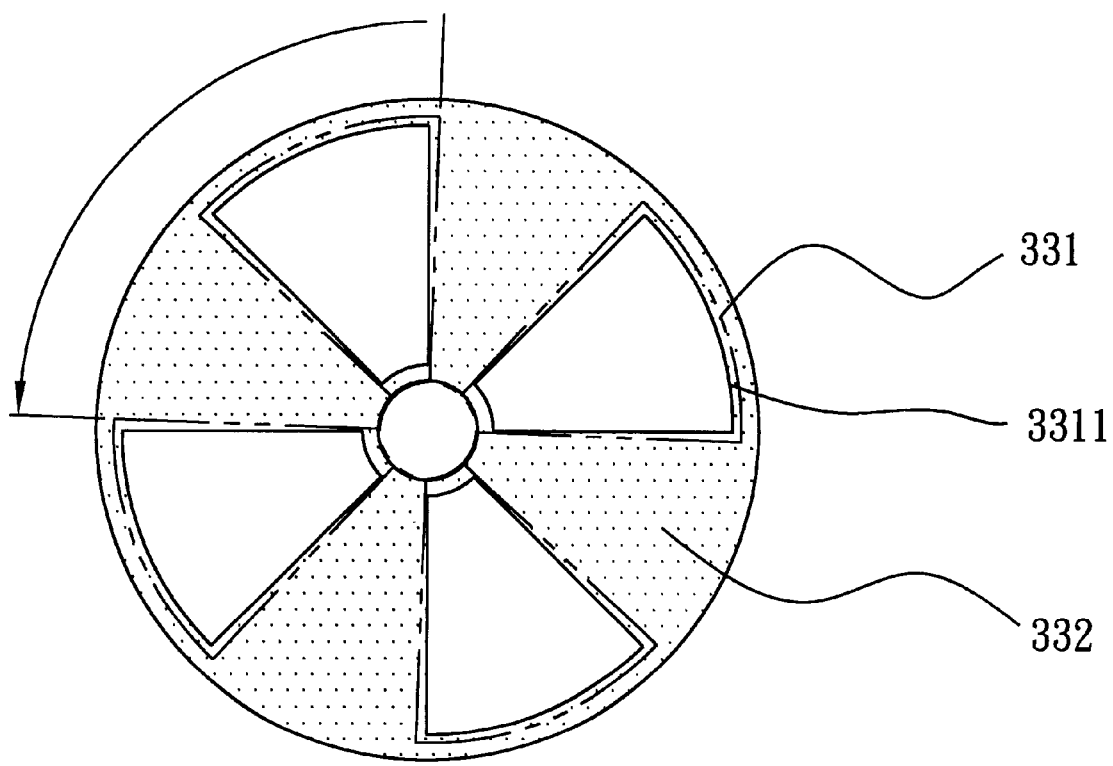
FIG. 13 is an illustration of an example of variation of opening and closing for the exhausted material for the material-handling apparatus of the moisture content tester of another embodiment according to the present utility model.

Second one (as shown in FIG. 13), the material-blocking lid 332 may also be a blade type to open and close the material-feeding dipper 331 by rotating the blade an appropriate angle.

In addition, the material-exhausting dipper 34 may also use a connection pipe to exhaust the cereals after being measured out the apparatus.

Preferably, the apparatus further includes an active lid 35, which is arranged at the upper portion of the material-handling apparatus 33 and connected with the machine shell 31. When the objet to be tested is set into the material-feeding dipper 331, the active lid 35 is closed for ensuring the measuring accuracy for the object to be tested.

However, a kind of material-handling apparatus 33 of the moisture content tester according to the present utility model may also transmit the measured values via a microprocessor through a signal line to the mainframe of a computer for facilitating the analysis of data.

What is claimed is:

1. A moisture content tester for non-destructive multipurpose testing for, testing water containment on objects to be tested, and which is carried out in a single machine and has a material-handling apparatus that may remove the material after being tested therefrom, comprising:

a shell body, having an accommodation space;

a circuit plate, positioned in the accommodation space, and having a circuit for processing temperature sensing data, generate high frequency, and receive high frequency;

a temperature compensation temperature-sensing bar, of which one end is connected to the circuit plate and another end is protruded out the shell body for sensing of temperature value;

at least an emitting pole, having one end connected to the circuit plate and protruded out of the shell body through one side of the shell body, and which is coupled to the circuit capable of generating high frequency to make a high frequency wave be emitted from the emitting pole-plate;

at least a receiving pole protruding out of the shell body spaced from the emitting pole, and coupled to the circuit capable of receiving high frequency to make the high frequency emitted from the emitting pole and the high frequency received by the circuit being converted into high frequency signals; and a controlling unit, which is coupled to the circuit plate, and the high frequency signals received by the receiving pole and temperature value sensed by the temperature compensation temperature-sensing bar are all transferred to the controlling unit through the circuit plate, and the corresponding value of water containment can be calculated out by the controlling unit according to the high frequency signals and in matching with the temperature value; wherein, the emitting pole is shown as a fin-shaped structure, of which upper side has an inclining side;

one side of the shell body is shown as an opening shape and is an opening side, through which the circuit plate is made to be set into the accommodation space, and the receiving pole is shown as a covering plate shape, which may just be covered on the opening side of the shell body, and on the receiving pole, there is arranged with an opening and at least a fin, and the position and form of the opening is matched with the emitting pole to provide the inclining side of the emitting pole to protrude through the receiving pole, and the extension direction of protrusion of the fin is matched with the receiving pole, and the fin is kept an appropriate distance with the receiving pole; wherein, the fin is larger than the emitting pole, and there is an inclining edge on the upper side of the fin;

a further included insulation plate, which is located between the receiving pole and the circuit plate, and on which an opening groove is arranged at a position corresponding to the emitting pole for providing the inclining side of the emitting pole to protrude out the insulation plate, and the circumferential edge of the opening groove is arranged with protruding edge to make itself be just set in between the opening of the receiving pole and the emitting pole to prevent the emitting pole and the receiving pole from contacting to each other;

a displaying unit further arranged on the controlling unit at least displays the sensed temperature value and water containment value.

2. A moisture content tester for non-destructive multipurpose testing according to claim 1, wherein the machine apparatus needed to proceed moisture content test is a drying apparatus that may proceed drying job on the object to be tested:

the controlling unit is further connected to the drying apparatus and may control the drying motion of the drying apparatus according to the water containment value measured by the moisture content tester.

3. A moisture content tester for non-destructive multipurpose testing according to claim 2, wherein the drying motion of the drying apparatus controlled by the controlling unit includes:

when the water containment value is higher than a first predetermined water containment value, then the drying motion of drying apparatus is kept continuous, but when the water containment value is smaller than the first predetermined water containment value, then the drying motion is stopped;

when the water containment value is higher than a second predetermined water containment value, then the output of the drying firepower of the drying apparatus is enhanced; wherein, the displaying contents of the displaying unit further includes: the first predetermined water containment value, the second predetermined water containment value, a time setting value that represents the controlling unit will directly stop the drying motion of the drying apparatus after a specific time period;

at least a stove and a fan are arranged on the drying apparatus, and by the fan with the manners of blowing or sucking, the hot air generated by the stove is sent through the object to be tested that is accommodated inside the drying apparatus for proceeding its drying motion; further, the displaying contents of the displaying unit of the controlling unit further include: a measured wind power value, a first predetermined wind power value, and a second wind power value that all indicate the situations in the interior of the drying apparatus;

when the measured wind power value is smaller than the first predetermined wind power value, the controlling power will send off alarm signal, and when the measured wind power value is smaller than the second predetermined wind power value, the motion of the drying apparatus will be stopped.

4. A moisture content tester for non-destructive multipurpose testing according to claim 1, wherein material-handling apparatus includes:

a machine shell;

a supporting rack, which is arranged in the machine shell;

a material-handling apparatus, which is arranged at the upper portion of the supporting rack and includes:

a material-feeding dipper that accommodates the object to be tested and has an emitting pole, a receiving pole, and a lower opening; the emitting pole emits a high frequency that is received by the receiving pole, and the moisture content of the object to be tested being measured by the capacitance difference between two poles, and the lower opening may remove the object to be tested therefrom;

at least a material-blocking lid, which may be used for opening and closing the lower opening; and, a material-exhausting dipper, which is used for receiving the object to be tested that is exhausted from the material-feeding dipper;

wherein the material-handling apparatus further includes at least an electromagnetic device and a material-blocking lid that has a connection end an a rotation axle, and the electromagnetic device is arranged at the upper portion of the supporting rack and at one side of the material-feeding dipper, and the connection end of the material-blocking lid is connected with the electromagnetic device, and the rotation axle is fixed at the supporting rack, and the electromagnetic device is actuated to execute the opening and closing motions for the material-blocking lid by taking the rotation axle that is fixed at the supporting rack as its rotation axle.

* * * * *